United States Patent [19]

Hoffbeck

[11] Patent Number: 5,618,987
[45] Date of Patent: Apr. 8, 1997

[54] INBRED MAIZE LINE PH42B

[75] Inventor: Loren J. Hoffbeck, Tipton, Ind.

[73] Assignee: Pioneer Hi-Bred International, Inc., Des Moines, Iowa

[21] Appl. No.: 522,670

[22] Filed: Sep. 1, 1995

[51] Int. Cl.⁶ .............................. A01H 1/02; A01H 4/00; A01H 5/00; C12N 5/04

[52] U.S. Cl. ................ 800/200; 800/250; 800/DIG. 56; 47/58; 47/DIG. 1; 435/412

[58] Field of Search ........................ 800/200, 205, 800/235, 250, DIG. 56; 435/240.1, 240.4, 240.47, 240.49, 240.5; 47/58.01, 58.03, 58, DIG. 1

[56] References Cited

U.S. PATENT DOCUMENTS 5,354,941  10/1994  Segebart ............................. 800/200

FOREIGN PATENT DOCUMENTS 160390  11/1985  European Pat. Off.

OTHER PUBLICATIONS

Conger, B.V., et al. (1987) "Somatic Embryogenesis From Cultured Leaf Segments of Zea Mays", *Plant Cell Reports*, 6:345–347.

Duncan, D.R., et al. (1985) "The Production of Callus Capable of Plant Regeneration From Immature Embryos of Numerous Zea Mays Genotypes", *Planta*, 165:322–332.

Edallo, et al. (1981) "Chromosomal Variation and Frequency of Spontaneous Mutation Associated with in Vitro Culture and Plant Regeneration in Maize", *Maydica*, XXVI: 39–56.

Green, et al., (1975) "Plant Regeneration in Tissue Cultures of Maize", *Crop Science*, vol. 15, pp. 417–421.

Green, C.E. et al. (1982) "Plant Regeneration in Tissue Cultures of Maize" *Maize for Biological Research*, pp. 367–372.

Meghji, M.R., et al. (1984). "Inbreeding Depression, Inbred & Hybrid Grain Yields, and Other Traits of Maize Genotypes Representing Three Eras", *Crop Science*, vol. 24, pp. 545–549.

Phillips, et al. (1988) "Cell/Tissue Culture and In Vitro Manipulation", *Corn & Corn Improvement*, 3rd Ed., ASA Publication, No. 18, pp. 345–387.

Poehlman et al., (1995) *Breeding Field Crop*, 4th Ed., Iowa State University Press, Ames, IA., pp. 132–155 and 321–344.

Rao, K.V., et al., (1986) "Somatic Embryogenesis in Glume Callus Cultures", *Maize Genetics Cooperative Newsletter*, No. 60, pp. 64–65.

Sass, John F. (1977) "Morphology", *Corn & Corn Improvement*, ASA Publication. Madison, Wisconsin, pp. 89–109.

Songstad, D.D. et al. (1988) "Effect of ACC (1-aminocyclopropane-1-carboxylic acid), Silver Nitrate & Norbonadiene on Plant Regeneration From Maize Callus Cultures", *Plant Cell Reports*, 7:262–265.

Tomes, et al. (1985) "The Effect of Parental Genotype on Initiation of Embryogenic Callus From Elite Maize (Zea Mays L.) Germplasm", *Theor. Appl. Genet.*, vol. 70, pp. 505–509.

Troyer, et al. (1985) "Selection for Early Flowering in Corn: 10 Late Synthetics", *Crop Science*, vol. 25, pp. 695–697.

Umbeck, et al. (1983) "Reversion of Male-Sterile T-Cytoplasm Maize to Male Fertility in Tissue Culture", *Crop Science*, vol. 23, pp. 584–588.

Wright, Harold (1980) "Commercial Hybrid Seed Production", *Hybridization of Crop Plants*, Ch. 8: 161–176.

Wych, Robert D. (1988) "Production of Hybrid Seed", *Corn and Corn Improvement*, Ch. 9, pp. 565–607.

Lee, Michael (1994) "Inbred Lines of Maize and Their Molecular Markers", *The Maize Handbook* Ch. 65:423–432.

Boppenmaier, et al., "Comparsons Among Strains of Inbreds for RFLPs", Maize Genetics Cooperative Newsletter, 65:1991, p. 90.

Coe et al. In Corn and Corn Improvement. Third Edition. Sprague et al., eds. American Society of Agronomy. Madison, WI. pp. 81–137.

Hallauer et al. In Corn and Corn Improvement. Third Edition. Sprague et al., eds. American Society of Agronomy. Madison, WI. pp: 482–564.

*Primary Examiner*—Erich E. Veitenheimer
*Attorney, Agent, or Firm*—Zarley, McKee, Thomte, Voorhees, & Sease

[57] ABSTRACT

An inbred maize line, designated PH42B, the plants and seeds of inbred maize line PH42B, methods for producing a maize plant produced by crossing the inbred line PH42B with itself or with another maize plant, and hybrid maize seeds and plants produced by crossing the inbred line PH42B with another maize line or plant.

14 Claims, No Drawings

5,618,987

INBRED MAIZE LINE PH42B

FIELD OF THE INVENTION

This invention is in the field of maize breeding, specifically relating to an inbred maize line designated PH42B.

BACKGROUND OF THE INVENTION

The goal of plant breeding is to combine in a single variety or hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Maize (zea mays L.), often referred to as corn in the United States, can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

A reliable method of controlling male fertility in plants offers the opportunity for improved plant breeding. This is especially true for development of maize hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid maize seed is typically produced by a male sterility system incorporating manual or mechanical detasseling. Alternate strips of two inbred varieties of maize are planted in a field, and the pollen-bearing tassels are removed from one of the inbreds (female). Providing that there is sufficient isolation from sources of foreign maize pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled fertile maize and CMS produced seed of the same hybrid are blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brat et al. and chromosomal translocations as described by Patterson in U.S. Pat. Nos. 3,861,709 and 3,710,511. These and all patents referred to are incorporated by reference. In addition to these methods, Albertsen et al., of Pioneer Hi-Bred, U.S. patent application Ser. No. 07/848,433, have developed a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329, 308 and PCT application PCT/CA90/00037 published as WO 90/08828).

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. : 4,936,904). Application of the gametocide, timing of the application and genotype specificity often limit the usefulness of the approach.

The use of male sterile inbreds is but one factor in the production of maize hybrids. The development of maize hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \to F_2$; $F_3 \to F_4$; $F_4 \to F_5$, etc.

Recurrent selection breeding, backcrossing for example, can be used to improve an inbred line. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation is then selfed to give pure breeding progeny for the gene(s) being transferred.

A single cross hybrid maize variety is the cross of two inbred lines, each of which has a genotype that complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid maize variety involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in maize, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)× (C×D). Much of the hybrid vigor exhibited by $F_1$ hybrids is lost in the next generation ($F_2$). Consequently, seed from hybrid varieties is not used for planting stock.

Maize is an important and valuable field crop. Thus, a continuing goal of plant breeders is to develop high-yielding maize hybrids that are agronomically sound based on stable inbred lines. The reasons for this goal are obvious: to maximize the amount of grain produced with the inputs used and minimize susceptibility of the crop to environmental stresses. To accomplish this goal, the maize breeder must select and develop superior inbred parental lines for producing hybrids. This requires identification and selection of genetically unique individuals that occur in a segregating population. The segregating population is the result of a combination of crossover events plus the independent assortment of specific combinations of alleles at many gene loci that results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population. Typically, however, the genotype of neither the parents nor the desired genotype is known in any detail.

In addition to the preceding problem, it is not known how the genotype will react with the environment. This genotype by environment interaction is an important, yet unpredictable, factor in plant breeding. A breeder of ordinary skill in the art cannot predict the genotype, how that genotype will interact with various environments or the resulting phenotypes of the developing lines, except perhaps in a very broad and general fashion. A breeder of ordinary skill in the art would also be unable to recreate the same line twice from the very same original parents as the breeder is unable to direct how the genomes combine or how they will interact with the environmental conditions. This unpredictability results in the expenditure of large amounts of research resources in the development of a superior new maize inbred line.

Pioneer research station staff propose about 400 to 500 new inbreds each year from over 2,000,000 pollinations. Of those proposed new inbreds, less than 50 and more commonly less than 30 are actually selected for commercial use.

SUMMARY OF THE INVENTION

According to the invention, there is provided a novel inbred maize line, designated PH42B. This invention thus relates to the seeds of inbred maize line PH42B, to the plants of inbred maize line PH42B, and to methods for producing a maize plant produced by crossing the inbred line PH42B with itself or another maize line. This invention further relates to hybrid maize seeds and plants produced by crossing the inbred line PH42B with another maize line.

DEFINITIONS

In the description and examples that follow, a number of terms are used herein. In order to provide a clear and consistent understanding of the specification and claims, including the scope to be given such terms, the following definitions are provided. NOTE: ABS is in absolute terms and % MN is percent of the mean for the experiments in which the inbred or hybrid was grown. These designators will follow the descriptors to denote how the values are to be interpreted. Below are the descriptors used in the data tables included herein.

ANT ROT=ANTHRACNOSE STALK ROT (*Colletotrichum graminicola*). A 1 to 9 visual rating indicating the resistance to Anthracnose Stalk Rot. A higher score indicates a higher resistance.

BAR PLT=BARREN PLANTS. The percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Yield of the grain at harvest in bushels per acre adjusted to 15.5% moisture.

CLN=CORN LETHAL NECROSIS. Synergistic interaction of maize chlorotic mottle virus (MCMV) in combination with either maize dwarf mosaic virus (MDMV-A or MDMV-B) or wheat streak mosaic virus (WSMV). A 1 to 9 visual rating indicating the resistance to Corn Lethal Necrosis. A higher score indicates a higher resistance.

COM RST=COMMON RUST (*Puccinia sorghi*). A 1 to 9 visual rating indicating the resistance to Common Rust. A higher score indicates a higher resistance.

DID=DRYDOWN. This represents the relative rate at which a hybrid will reach acceptable harvest moisture compared to other hybrids on a 1–9 rating scale. A high score indicates a hybrid that dries relatively fast while a low score indicates a hybrid that dries slowly.

DIP ERS=DIPLODIA EAR MOLD SCORES (*Diplodia maydis* and *Diplodia macrospora*). A 1 to 9 visual rating indicating the resistance to Diplodia Ear Mold. A higher score indicates a higher resistance.

DRP EAR=DROPPED EARS. A measure of the number of dropped ears per plot and represents the percentage of plants that did not drop ears prior to harvest.

D/T=DROUGHT TOLERANCE. This represents a 1–9 rating for drought tolerance, and is based on data obtained under stress conditions. A high score indicates good drought tolerance and a low score indicates poor drought tolerance.

EAR HT=EAR HEIGHT. The ear height is a measure from the ground to the highest placed developed ear node attachment and is measured in inches.

EAR MLD=General Ear Mold. Visual rating (1–9 score) where a "1" is very susceptible and a "9" is very resistant. This is based on overall rating for ear mold of mature ears without determining the specific mold organism, and may not be predictive for a specific ear mold.

EAR SZ=EAR SIZE. A 1 to 9 visual rating of ear size. The higher the rating the larger the ear size.

ECB 1LF=EUROPEAN CORN BORER FIRST GENERATION LEAF FEEDING (*Ostrinia nubilalis*). A 1 to 9 visual rating indicating the resistance to preflowering leaf feeding by first generation European Corn Borer. A higher score indicates a higher resistance.

ECB 2IT=EUROPEAN CORN BORER SECOND GENERATION INCHES OF TUNNELING (*Ostrinia nubilalis*). Average inches of tunneling per plant in the stalk.

ECB 2SC=EUROPEAN CORN BORER SECOND GENERATION (*Ostrinia nubilalis*). A 1 to 9 visual rating indicating post flowering degree of stalk breakage and other evidence of feeding by European Corn Borer, Second Generation. A higher score indicates a higher resistance.

ECB DPE=EUROPEAN CORN BORER DROPPED EARS (*Ostrinia nubilalis*). Dropped ears due to European Corn Borer. Percentage of plants that did not drop ears under second generation corn borer infestation.

EST CNT=EARLY STAND COUNT. This is a measure of the stand establishment in the spring and represents the number of plants that emerge on per plot basis for the inbred or hybrid.

EYE SPT=Eye Spot (*Kabatiella zeae* or *Aureobasidium zeae*). A 1 to 9 visual rating indicating the resistance to Eye Spot. A higher score indicates a higher resistance.

FUS ERS=FUSARIUM EAR ROT SCORE (*Fusarium moniliforme* or *Fusarium subglutinans*). A 1 to 9 visual rating indicating the resistance to Fusarium ear rot. A higher score indicates a higher resistance.

GDU=Growing Degree Units. Using the Barger Heat Unit Theory, which assumes that maize growth occurs in the temperature range 50° F.–86° F. and that temperatures outside this range slow down growth; the maximum daily heat unit accumulation is 36 and the minimum daily heat unit accumulation is 0. The seasonal accumulation of GDU is a major factor in determining maturity zones.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(Max.\ temp. + Min.\ temp.)}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GIB ERS=GIBBERELLA EAR ROT (PINK MOLD) (*Gibberella zeae*). A 1 to 9 visual rating indicating the resistance to Gibberella Ear Rot. A higher score indicates a higher resistance.

GLF SPT=Gray Leaf Spot (*Cercospora zeae-maydis*). A 1 to 9 visual rating indicating the resistance to Gray Leaf Spot. A higher score indicates a higher resistance.

GOS WLT=Goss' Wilt (*Corynebacterium nebraskense*). A 1 to 9 visual rating indicating the resistance to Goss' Wilt. A higher score indicates a higher resistance.

GRN APP=GRAIN APPEARANCE. This is a 1 to 9 rating for the general appearance of the shelled grain as it is harvested based on such factors as the color of harvested grain, any mold on the grain, and any cracked grain. High scores indicate good grain quality.

H/POP=YIELD AT HIGH DENSITY. Yield ability at relatively high plant densities on 1–9 relative rating system with a higher number indicating the hybrid responds well to high plant densities for yield relative to other hybrids. A 1, 5, and 9 would represent very poor, average, and very good yield response, respectively, to increased plant density.

HC BLT=HELMINTHOSPORIUM CARBONUM LEAF BLIGHT (*Helminthosporium carbonum*). A 1 to 9 visual rating indicating the resistance to Helminthosporium infection. A higher score indicates a higher resistance.

HD SMT=HEAD SMUT (*Sphacelotheca reiliana*). This score indicates the percentage of plants not infected.

INC D/A=GROSS INCOME (DOLLARS PER ACRE). Relative income per acre assuming drying costs of two cents per point above 15.5 percent harvest moisture and current market price per bushel.

INCOME/ACRE. Income advantage of hybrid to be patented over other hybrid on per acre basis.

INC ADV=GROSS INCOME ADVANTAGE. GROSS INCOME advantage of variety #1 over variety #2.

L/POP=YIELD AT LOW DENSITY. Yield ability at relatively low plant densities on a 1–9 relative system with a higher number indicating the hybrid responds well to low plant densities for yield relative to other hybrids. A 1, 5, and 9 would represent very poor, average, and very good yield response, respectively, to low plant density.

MDM CPX=MAIZE DWARF MOSAIC COMPLEX (MDMV=Maize Dwarf Mosaic Virus and MCDV=Maize Chlorotic Dwarf Virus). A 1 to 9 visual rating indicating the resistance to Maize Dwarf Mosaic Complex. A higher score indicates a higher resistance.

MST=HARVEST MOISTURE. The moisture is the actual percentage moisture of the grain at harvest.

MST ADV=MOISTURE ADVANTAGE. The moisture advantage of variety #1 over variety #2 as calculated by: MOISTURE of variety #2—MOISTURE of variety #1=MOISTURE ADVANTAGE of variety #1.

NLF BLT=Northern Leaf Blight (*Helminthosporium turcicum* or *Exserohilum turcicum*). A 1 to 9 visual rating indicating the resistance to Northern Leaf Blight. A higher score indicates a higher resistance.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete.

It should be understood that the inbred can, through routine manipulation of cytoplasmic or other factors, be produced in a male-sterile form. Such embodiments are also contemplated within the scope of the present claims.

POP K/A=PLANT POPULATIONS. Measured as 1000s per acre.

POP ADV=PLANT POPULATION ADVANTAGE. The plant population advantage of variety #1 over variety #2 as calculated by PLANT POPULATION of variety #2—PLANT POPULATION of variety #1=PLANT POPULATION ADVANTAGE of variety #1.

PRM=PREDICTED RELATIVE MATURITY. This trait, predicted relative maturity, is based on the harvest moisture of the grain. The relative maturity rating is based on a known set of checks and utilizes standard linear regression analyses and is also referred to as the Comparative Relative Maturity Rating System that is similar to the Minnesota Relative Maturity Rating System.

PRM SHD=A relative measure of the growing degree units (GDU) required to reach 50% pollen shed. Relative values are predicted values from the linear regression of observed GDU's on relative maturity of commercial checks.

RT LDG=ROOT LODGING. Root lodging is the percentage of plants that do not root lodge; plants that lean from the vertical axis at an approximately 30° angle or greater would be counted as root lodged.

RTL ADV=ROOT LODGING ADVANTAGE. The root lodging advantage of variety #1 over variety #2.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A maize breeder may utilize his or her own set of traits for the selection index. One of the traits that is almost always included is yield. The selection index data presented in the tables represent the mean value averaged across testing stations.

SLF BLT=SOUTHERN LEAF BLIGHT (*Helminthosporium maydis* or *Bipolaris maydis*). A 1 to 9 visual rating indicating the resistance to Southern Leaf Blight. A higher score indicates a higher resistance.

SOU RST=SOUTHERN RUST (*Puccinia polysora*). A 1 to 9 visual rating indicating the resistance to Southern Rust. A higher score indicates a higher resistance.

STA GRN=STAY GREEN. Stay green is the measure of plant health near the time of black layer formation (physiological maturity). A high score indicates better late-season plant health.

STD ADV=STALK STANDING ADVANTAGE. The advantage of variety #1 over variety #2 for the trait STK CNT.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

STW WLT=Stewart's Wilt (*Erwinia stewartii*). A 1 to 9 visual rating indicating the resistance to Stewart's Wilt. A higher score indicates a higher resistance.

TAS BLS=TASSEL BLAST. A 1 to 9 visual rating was used to measure the degree of blasting (necrosis due to heat stress) of the tassel at the time of flowering. A would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as a percentage of tillers: number of tillers per plot divided by number of plants per plot.

TST WT=TEST WEIGHT (UNADJUSTED). The measure of the weight of the grain in pounds for a given volume (bushel).

TST WTA=TEST WEIGHT ADJUSTED. The measure of the weight of the grain in pounds for a given volume (bushel) adjusted for 15.5 percent moisture.

TSW ADV=TEST WEIGHT ADVANTAGE. The test weight advantage of variety over variety #2.

WIN M %=PERCENT MOISTURE WINS.

WIN Y %=PERCENT YIELD WINS.

YLD=YIELD. It is the same as BU ACR ABS.

YLD ADV=YIELD ADVANTAGE. The yield advantage of variety #1 over variety #2 as calculated by: YIELD of variety #1—YIELD variety #2=yield advantage of variety #1.

YLD SC=YIELD SCORE. A 1 to 9 visual rating was used to give a relative rating for yield based on plot ear piles. The higher the rating the greater visual yield appearance.

DETAILED DESCRIPTION OF THE INVENTION

Inbred maize lines are typically developed for use in the production of hybrid maize lines. Inbred maize lines need to be highly homogeneous, homozygous and reproducible to be useful as parents of commercial hybrids. There are many analytical methods available to determine the homozygotic and phenotypic stability of these inbred lines.

The oldest and most traditional method of analysis is the observation of phenotypic traits. The data is usually collected in field experiments over the life of the maize plants to be examined. Phenotypic characteristics most often observed are for traits associated with plant morphology, ear and kernel morphology, insect and disease resistance, maturity, and yield.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The most widely used of these laboratory techniques are Isozyme Electrophoresis and RFLPs as discussed in Lee, M., "Inbred Lines of Maize and Their Molecular Markers," The Maize Handbook, (Springer-Verlag, New York, Inc. 1994, at 423–432) incorporated herein by reference. Isozyme Electrophoresis is a useful tool in determining genetic composition, although it has relatively low number of available markers and the low number of allelic variants among maize inbreds. RFLPs have the advantage of revealing an exceptionally high degree of allelic variation in maize and the number of available markers is almost limitless.

Maize RFLP linkage maps have been rapidly constructed and widely implemented in genetic studies. One such study is described in Boppenmaier, et al., "Comparisons among strains of inbreds for RFLPs", Maize Genetics Cooperative Newsletter, 65:1991, pg. 90, is incorporated herein by reference. This study used 101 RFLP markers to analyze the patterns of 2 to 3 different deposits each of five different inbred lines. The inbred lines had been selfed from 9 to 12 times before being adopted into 2 to 3 different breeding programs. It was results from these 2 to 3 different breeding programs that supplied the different deposits for analysis. These five lines were maintained in the separate breeding programs by selfing or sibbing and rogueing off-type plants for an additional one to eight generations. After the RFLP analysis was completed, it was determined the five lines showed 0–2% residual heterozygosity. Although this was a relatively small study, it can be seen using RFLPs that the lines had been highly homozygous prior to the separate strain maintenance.

Inbred maize line PH42B is a yellow, dent maize inbred that is best suited as a female in crosses for producing first generation $F_1$ maize hybrids. Inbred maize line PH42B is best adapted to the Central Corn Belt and the Northcentral and Northeast regions of the United States and can be used to produce hybrids from approximately 108 relative maturity based on the Comparative Relative Maturity Rating System for harvest moisture of grain. Inbred maize line PH42B, as an inbred per se, yields well for its maturity, has a favorable kernel size for planting, and has almost no tillers. In hybrid combination, PH42B demonstrates high grain yield and dries fast in the field. PH42B hybrids also demonstrate excellent staygreen.

The inbred has shown uniformity and stability within the limits of environmental influence for all the traits as described in the Variety Description Information (Table 1) that follows. The inbred has been self-pollinated and ear-rowed a sufficient number of generations with careful attention paid to uniformity of plant type to ensure the homozygosity and phenotypic stability necessary to use in commercial production. The line has been increased both by hand and in isolated fields with continued observation for uniformity. No variant traits have been observed or are expected in PH42B.

Inbred maize line PH42B, being substantially homozygous, can be reproduced by planting seeds of the line, growing the resulting maize plants under self-pollinating or sib-pollinating conditions with adequate isolation, and harvesting the resulting seed, using techniques familiar to the agricultural arts.

TABLE 1

VARIETY DESCRIPTION INFORMATION
INBRED = PH42B

Type: Dent
A. Maturity: Average cross maturity zones. Zone: 0
   GDU Shed: 1430
   GDU Silk: 1440
   No. Reps: 47
B. Plant Characteristics:
   Length of top ear internode: 16 cm
   Number of ears per stalk: Single Plant Height: 224.5 cm.
   Ear height (to base of top ear): 79 cm
   Number of tillers: None
   Cytoplasm type: Normal
C. Leaf:
   Color: (B14) Dark Green*
   Angle from Stalk: 30–60 degrees
   Marginal Waves: (WF9) Few
   Number of Leaves (mature plants): 21
   Sheath Pubescence: (W22) Light
   Longitudinal Creases: (PA11) Many
   Length (Ear node leaf): 86 cm
   Width (widest point, ear node leaf): 10 cm
D. Tassel:
   Number lateral branches: 1
   Peduncle Length (top leaf to basal branches): 24 cm
   Anther Color: Yellow*
   Glume Color: Green*
E. Ear (Husked Ear Data Except When Stated Otherwise):
   Length: 18 cm
   Weight: 141 gm
   Mid-point Diameter: 44 mm
   Silk Color: Green*
   Husk Extension (Harvest stage): Medium (Barely Covering Ear)
   Husk Leaf: Long (>15 cm)
   Taper of Ear: Average
   Position of Shank (dry husks): Upright
   Kernel Rows: Distinct, Slightly curved Number: 16
   Husk Color (fresh): Light green*
   Husk Color (dry): Buff*
   Shank Length: 19 cm
   Shank (No. of internodes): 11
F. Kernel (Dried):
   Size (from ear mid-point)
   Length: 11 mm
   Width: 8 mm
   Thick: 5 mm
   Shape Grade (% rounds) (31% medium round) 20–40
   Pericarp Color: Colorless*
   Aleurone Color: Homozygous Yellow*
   Endosperm Color: Yellow*
   Endosperm Type: Normal Starch
   Gm Wt/100 Seeds (unsized): 31 gm
G. Cob:
   Diameter at mid-point: 25 mm
   Strength: Strong
   Color: Red*

TABLE 1-continued

VARIETY DESCRIPTION INFORMATION
INBRED = PH42B

H. Diseases:
   Corn Lethal Necrosis (MCMV=Maize Chlorotic Mottle
   Virus and MDMV=Maize
   Dwarf Mosaic Virus): Intermediate
   S. Leaf Blight (*B. maydis*): Intermediate
   N. Leaf Blight (*E. turcicum*): Highly Resistant
   Common Rust (*P. sorghi*): Resistant
   Eye Spot (*K. zeae*): Resistant
   Gray Leaf Spot (*C. zeae*): Intermediate
   Fusarium Ear Mold (*F. moniliforme*): Susceptible
I. Insects:
   European Corn Borer-1 Leaf Damage (Preflowering):
   Intermediate
   European Corn Borer-2 (Post-flowering): Intermediate
   The above descriptions are based on a scale of 1-9, 1 being
   highly susceptible, 9 being highly resistant.
   S (Susceptible): Would generally represent a score of 1-3.
   I (Intermediate): Would generally represent a score of 4-5.
   R (Resistant): Would generally represent a score of 6-7.
   H (Highly Resistant) Would generally represent a score of
   8-9. Highly resistant does not imply the inbred is immune.
J. Varieties Most Closely Resembling: PHT11 and PHP38

*In interpreting the foregoing color designations, reference may be had to the Munsell Glossy Book of Color, a standard color reference.
Data for Items B, C, D, E, F, and G is based primarily on a maximum of 2 reps from Johnston, Iowa grown in 1994, plus description information from the maintaining station.

INDUSTRIAL APPLICABILITY

This invention also is directed to methods for producing a maize plant by crossing a first parent maize plant with a second parent maize plant wherein the first or second parent maize plant is an inbred maize plant of the line PH42B. Further, both first and second parent maize plants can come from the inbred maize line PH42B. Thus, any such methods using the inbred maize line PH42B are part of this invention: selfing, backcrosses, hybrid production, crosses to populations, and the like. All plants produced using inbred maize line PH42B as a parent are within the scope of this invention. Advantageously, the inbred maize line is used in crosses with other, different, maize inbreds to produce first generation ($F_1$) maize hybrid seeds and plants with superior characteristics.

As used herein, the term plant includes plant cells, plant protoplasts, plant cell tissue cultures from which maize plants can be regenerated, plant calli, plant clumps, and plant cells that are intact in plants or parts of plants, such as embryos, pollen, ovules, flowers, kernels, ears, cobs, leaves, husks, stalks, roots, root tips, anthers, silk and the like.

Duncan, Williams, Zehr, and Widholm, Planta (1985) 165:322–332 reflects that 97% of the plants cultured that produced callus were capable of plant regeneration. Subsequent experiments with both inbreds and hybrids produced 91% regenerable callus that produced plants. In a further study in 1988; Songstad, Duncan & Widholm in *Plant Cell Reports* (1988), 7:262–265 reports several media additions that enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter*, 60:64–65 (1986), refers to somatic embryogenesis from glume callus cultures and B. V. Conger, et al., *Plant Cell Reports*, 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize is described in European Patent Application, publication 160,390, incorporated herein by reference. Maize tissue culture procedures are also described in Green and Rhodes, "Plant Regeneration in Tissue Culture of Maize," *Maize for Biological Research* (Plant Molecular Biology Association, Charlottesville, Va. 1982, at 367–372) and in Duncan, et al., "The Production of Callus Capable of Plant Regeneration from Immature Embryos of Numerous Zea Mays Genotypes," 165 *Planta* 322–332 (1985). Thus, another aspect of this invention is to provide cells which upon growth and differentiation produce maize plants having the physiological and morphological characteristics of inbred line PH42B.

Maize is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry: for example, stalks and husks are made into paper and wallboard and cobs are used for fuel and to make charcoal.

The seed of inbred maize line PH42B, the plant produced from the inbred seed, the hybrid maize plant produced from the crossing of the inbred, hybrid seed, and various parts of the hybrid maize plant can be utilized for human food, livestock feed, and as a raw material in industry.

PERFORMANCE EXAMPLES OF PH42B

In the examples that follow, the traits and characteristics of inbred maize line PH42B are presented as an inbred per se and in hybrid combination. The data collected on inbred maize line PH42B is presented for key characteristics and traits.

The inbred per se results in Table 2A compare PH42B to PHP38, a close comparison line for this maturity. The results show PH42B is significantly higher yielding than PHP38. In addition, PH42B has a significantly lower harvest moisture than PHP38. Inbred PH42B also demonstrates a better staygreen score than that of PHP38.

Table 2B compares PH42B to its parent, PHT11. The inbred per se results show PH42B is significantly higher yielding than PHT11. In addition, PH42B has a significantly higher staygreen score than PHT11.

Table 3A compares the general combining abilities of PH42B and PHP38. The PH42B hybrids are higher yielding with a lower harvest moisture than the PHP38 hybrids. Both PH42B and PHP38 hybrids demonstrate good staygreen scores.

The general combining ability results in Table 3B compare PH42B to PHT11 in hybrid combination. The PH42B hybrids are higher yielding with significantly higher staygreen scores than the PHT11 hybrids. Both PH42B and PHT11 have lower harvest moisture levels.

Table 4A compares the specific combining abilities of PH42B and PHP38 in hybrid combination with PHN46. Both hybrids have similar high yields, however, the PH42B hybrid has significantly lower harvest moisture. Both hybrids demonstrate very good staygreen.

Table 4B compares the specific combining abilities of PH42B and PHT11 in hybrid combination with PHN46. The PH42B hybrid demonstrates a high yield that is somewhat higher than the PHT11 hybrid. Although the PHT11 hybrid has a lower harvest moisture, both hybrids are below the mean. The PH42B hybrid has a far superior staygreen score that is statistically significant at the 99% probability level.

TABLE 2A

PAIRED INBRED COMPARISON DATA
VARIETY #1 = PH42B
VARIETY #2 = PHP38

| | VAR # | BU ACR ABS | BU ACR % MN | MST ABS | TST WT ABS | SDG VGR ABS | EST CNT ABS | TIL LER ABS | GDU SHD ABS | GDU SLK ABS |
|---|---|---|---|---|---|---|---|---|---|---|
| TOTAL SUM | 1 | 102.1 | 122 | 17.3 | 57.1 | 5.5 | 28.3 | 0.8 | 143.1 | 144.2 |
| | 2 | 77.8 | 94 | 19.0 | 59.1 | 6.2 | 27.2 | 1.4 | 145.6 | 146.8 |
| | LOCS | 11 | 11 | 16 | 11 | 43 | 63 | 40 | 56 | 56 |
| | REPS | 22 | 22 | 27 | 22 | 51 | 88 | 50 | 60 | 60 |
| | DIFF | 24.3 | 28 | 1.8 | 1.9 | 0.7 | 1.1 | 0.6 | 2.4 | 2.6 |
| | PROB | .000# | .000# | .003# | .031+ | .001# | .043+ | .133 | .000# | .000# |

| | VAR # | POL SC ABS | TAS SZ ABS | PLT HT ABS | EAR HT ABS | RT LDG ABS | STA GRN ABS | STK LDG ABS | BRT STK ABS | GRN APP ABS |
|---|---|---|---|---|---|---|---|---|---|---|
| TOTAL SUM | 1 | 2.3 | 1.8 | 84.0 | 32.8 | 82.3 | 6.7 | 97.1 | 93.1 | 6.2 |
| | 2 | 5.6 | 5.3 | 79.6 | 31.9 | 100.0 | 5.4 | 98.4 | 93.5 | 7.8 |
| | LOCS | 21 | 25 | 24 | 23 | 6 | 20 | 7 | 10 | 3 |
| | REPS | 22 | 26 | 31 | 29 | 6 | 28 | 13 | 10 | 6 |
| | DIFF | 3.3 | 3.5 | 4.4 | 1.0 | 17.7 | 1.3 | 1.3 | 0.4 | 1.6 |
| | PROB | .000# | .000# | .001# | .331 | .102 | .012+ | .592 | .903 | .321 |

| | VAR # | SCT GRN ABS | EAR SZ ABS | TEX EAR ABS | EAR MLD ABS | BAR PLT ABS | DRP EAR ABS | GLF SPT ABS | SLF BLT ABS | STW WLT ABS |
|---|---|---|---|---|---|---|---|---|---|---|
| TOTAL SUM | 1 | 6.5 | 6.4 | 4.3 | 6.8 | 91.6 | 100.0 | 4.3 | 4.0 | 7.0 |
| | 2 | 6.4 | 5.3 | 6.4 | 7.7 | 92.2 | 99.8 | 3.7 | 6.2 | 4.0 |
| | LOCS | 13 | 11 | 9 | 11 | 36 | 4 | 6 | 2 | 1 |
| | REPS | 14 | 11 | 9 | 12 | 40 | 8 | 6 | 2 | 1 |
| | DIFF | 0.2 | 1.1 | 2.1 | 0.9 | 0.5 | 0.2 | 0.6 | 2.2 | 3.0 |
| | PROB | .753 | .010+ | .001# | .064* | .790 | .391 | .396 | .234 | |

| | VAR # | FUS ERS ABS | EYE SPT ABS | COM RST ABS | ECB 1LF ABS | ECB 2SC ABS |
|---|---|---|---|---|---|---|
| TOTAL SUM | 1 | 3.3 | 6.5 | 5.3 | 4.7 | 4.0 |
| | 2 | 5.3 | 5.5 | 5.7 | 4.0 | 5.7 |
| | LOCS | 4 | 2 | 3 | 7 | 3 |
| | REPS | 4 | 2 | 3 | 7 | 4 |
| | DIFF | 2.0 | 1.0 | 0.3 | 0.7 | 1.7 |
| | PROB | .161 | .000# | .667 | .140 | .300 |

\* 10% SIG
+ = 5% SIG
# = 1% SIG

TABLE 2B

PAIRED INBRED COMPARISON DATA
VARIETY #1 = PH42B
VARIETY #2 = PHT11

| | VAR # | BU ACR ABS | BU ACR % MN | MST ABS | TST WT ABS | SDG VGR ABS | EST CNT ABS | TIL LER ABS | GDU SHD ABS | GDU SLK ABS |
|---|---|---|---|---|---|---|---|---|---|---|
| TOTAL SUM | 1 | 97.1 | 118 | 23.0 | 54.7 | 5.4 | 35.5 | 0.9 | 142.4 | 143.9 |
| | 2 | 67.6 | 82 | 22.8 | 56.8 | 6.0 | 35.0 | 1.1 | 143.9 | 144.3 |
| | LOCS | 28 | 28 | 36 | 28 | 40 | 78 | 50 | 60 | 55 |

TABLE 2B-continued

PAIRED INBRED COMPARISON DATA
VARIETY #1 = PH42B
VARIETY #2 = PHT11

|  |  |  |  |  |  |  |  |  |  |
|---|---|---|---|---|---|---|---|---|---|
|  | REPS | 55 | 55 | 63 | 56 | 52 | 118 | 67 | 69 | 60 |
|  | DIFF | 30.1 | 37 | 0.2 | 2.1 | 0.5 | 0.5 | 0.2 | 1.5 | 0.4 |
|  | PROB | .000# | .000# | .675 | .000# | .015+ | .337 | .626 | .000# | .418 |

|  | VAR # | POL SC ABS | TAS SZ ABS | PLT HT ABS | EAR HT ABS | RT LDG ABS | STA GRN ABS | STK LDG ABS | BRT STK ABS | GRN APP ABS |
|---|---|---|---|---|---|---|---|---|---|---|
| TOTAL SUM | 1 | 2.5 | 1.6 | 84.6 | 33.8 | 79.6 | 7.0 | 97.3 | 92.3 | 5.6 |
|  | 2 | 2.3 | 1.6 | 94.1 | 36.8 | 67.7 | 5.0 | 90.5 | 92.5 | 6.6 |
|  | LOCS | 20 | 21 | 28 | 25 | 9 | 18 | 18 | 9 | 9 |
|  | REPS | 21 | 23 | 42 | 37 | 11 | 28 | 34 | 9 | 18 |
|  | DIFF | 0.1 | 0.0 | 9.5 | 3.0 | 11.9 | 2.0 | 6.8 | 0.1 | 1.0 |
|  | PROB | .582 | .715 | .000# | .000# | .237 | .001# | .024+ | .968 | .048+ |

|  | VAR # | SCT GRN ABS | EAR SZ ABS | TEX EAR ABS | EAR MLD ABS | BAR PLT ABS | DRP EAR ABS | GLF SPT ABS | NLF BLT ABS | SLF BLT ABS |
|---|---|---|---|---|---|---|---|---|---|---|
| TOTAL SUM | 1 | 6.5 | 6.7 | 4.5 | 7.1 | 93.1 | 99.8 | 4.3 | 8.5 | 4.0 |
|  | 2 | 6.4 | 4.0 | 6.8 | 7.4 | 89.3 | 99.4 | 3.2 | 7.0 | 3.0 |
|  | LOCS | 11 | 7 | 6 | 10 | 42 | 13 | 5 | 2 | 1 |
|  | REPS | 12 | 7 | 6 | 11 | 49 | 26 | 5 | 2 | 1 |
|  | DIFF | 0.1 | 2.7 | 2.3 | 0.3 | 3.8 | 0.4 | 1.1 | 1.5 | 1.0 |
|  | PROB | .846 | .013+ | .005# | .647 | .091* | .240 | .219 | .500 |  |

|  | VAR # | FUS ERS ABS | EYE SPT ABS | COM RST ABS | ECB 1LF ABS | ECB 2SC ABS |
|---|---|---|---|---|---|---|
| TOTAL SUM | 1 | 4.5 | 6.5 | 5.7 | 4.8 | 4.4 |
|  | 2 | 6.0 | 6.0 | 3.7 | 5.2 | 4.6 |
|  | LOCS | 2 | 2 | 3 | 6 | 4 |
|  | REPS | 2 | 2 | 4 | 6 | 6 |
|  | DIFF | 1.5 | 0.5 | 2.0 | 0.3 | 0.2 |
|  | PROB | .500 | .795 | .074* | .661 | .704 |

* = 10% SIG
+ = 5% SIG
# = 1% SIG

TABLE 3A

Average Inbred By Tester Performance Comparing PH42B To PHP38 Crossed To The Same Inbred Testers And Grown In The Same Experiments.

|  |  | SEL IND % MN | PRM ABS | BU ACR ABS | BU ACR % MN | PRM SHD ABS | MST % MN | TST WT ABS | SDG VGR % MN | EST CNT % MN |
|---|---|---|---|---|---|---|---|---|---|---|
| TOTAL SUM | REPLIC. | 20 | 23 | 186 | 186 | 20 | 213 | 115 | 98 | 118 |
|  | LOCS | 20 | 23 | 165 | 165 | 20 | 178 | 103 | 76 | 102 |
|  | PH42B | 106 | 108 | 176 | 105 | 113 | 93 | 56 | 96 | 99 |
|  | PHP38 | 103 | 110 | 171 | 102 | 111 | 100 | 56 | 120 | 102 |
|  | DIFF | 3 | 2 | 5 | 3 | 2 | 7 | 0 | 24 | 3 |
|  | PR > T | 0.15 | 0.00 | 0.01 | 0.01 | 0.00 | 0.00 | 0.01 | 0.00 | 0.04 |

|  |  | GDU SHD % MN | GDU SLK % MN | STK CNT % MN | PLT HT % MN | EAR HT % MN | RT LDG % MN | STA GRN % MN | STK LDG % MN | BRT STK % MN |
|---|---|---|---|---|---|---|---|---|---|---|
| TOTAL SUM | REPLIC. | 67 | 39 | 239 | 98 | 98 | 78 | 96 | 152 | 33 |
|  | LOCS | 51 | 28 | 193 | 86 | 86 | 59 | 84 | 127 | 26 |
|  | PH42B | 104 | 102 | 99 | 101 | 105 | 100 | 112 | 100 | 101 |
|  | PHP38 | 102 | 101 | 101 | 99 | 103 | 104 | 112 | 102 | 100 |
|  | DIFF | 1 | 1 | 1 | 2 | 2 | 4 | 0 | 2 | 1 |
|  | PR > T | 0.02 | 0.30 | 0.04 | 0.00 | 0.02 | 0.07 | 0.96 | 0.05 | 0.28 |

|  |  | GRN APP % MN | SLF BLT ABS | EYE SPT ABS | ECB DPE ABS | ECB 2SC ABS | DRP EAR % MN | GLF SPT ABS | NLF BLT ABS |
|---|---|---|---|---|---|---|---|---|---|
| TOTAL SUM | REPLIC. | 33 | 13 | 8 | 12 | 13 | 55 | 9 | 1 |
|  | LOCS | 33 | 5 | 7 | 12 | 11 | 46 | 9 | 1 |

TABLE 3A-continued

Average Inbred By Tester Performance Comparing PH42B To PHP38 Crossed To The Same Inbred Testers And Grown In The Same Experiments.

| | | | | | | | | |
|---|---|---|---|---|---|---|---|---|
| PH42B | 102 | 4 | 5 | 99 | 6 | 100 | 4 | 8 |
| PHP38 | 100 | 5 | 4 | 99 | 5 | 100 | 2 | 8 |
| DIFF | 1 | 1 | 1 | 0 | 0 | 0 | 1 | 0 |
| PR > T | 0.65 | 0.00 | 0.09 | 0.59 | 0.54 | 0.89 | 0.05 | |

*PR > T values are valid only for comparisons with Locs >= 10.

TABLE 3B

Average Inbred By Tester Performance Comparing PH42B To PHT11 Crossed To The Same Inbred Testers And Grown In The Same Experiments.

| | | SEL IND % MN | PRM ABS | BU ACR ABS | BU ACR % MN | PRM SHD ABS | MST % MN | TST WT ABS | SDG VGR % MN | EST CNT % MN |
|---|---|---|---|---|---|---|---|---|---|---|
| TOTAL SUM | REPLIC. | 16 | 19 | 172 | 172 | 17 | 192 | 111 | 88 | 113 |
| | LOCS | 16 | 19 | 155 | 155 | 17 | 165 | 101 | 69 | 99 |
| | PH42B | 106 | 107 | 177 | 105 | 113 | 94 | 55 | 95 | 99 |
| | PHT11 | 100 | 106 | 169 | 100 | 111 | 94 | 56 | 110 | 103 |
| | DIFF | 6 | 1 | 8 | 5 | 1 | 0 | 1 | 16 | 5 |
| | PR > T | 0.05 | 0.05 | 0.00 | 0.00 | 0.04 | 0.73 | 0.00 | 0.00 | 0.00 |

| | | GDU SHD % MN | GDU SLK % MN | STK CNT % MN | PLT HT % MN | EAR HT % MN | RT LDG % MN | STA GRN % MN | STK LDG % MN | BRT STK % MN |
|---|---|---|---|---|---|---|---|---|---|---|
| TOTAL SUM | REPLIC. | 60 | 35 | 218 | 86 | 86 | 72 | 80 | 135 | 24 |
| | LOCS | 46 | 26 | 179 | 77 | 77 | 55 | 72 | 115 | 19 |
| | PH42B | 104 | 102 | 100 | 101 | 105 | 101 | 115 | 100 | 102 |
| | PHT11 | 102 | 101 | 101 | 103 | 108 | 103 | 104 | 99 | 102 |
| | DIFF | 2 | 2 | 2 | 2 | 2 | 2 | 11 | 1 | 0 |
| | PR > T | 0.00 | 0.00 | 0.02 | 0.00 | 0.04 | 0.59 | 0.01 | 0.25 | 0.91 |

| | | GRN APP % MN | SLF BLT ABS | EYE SPT ABS | ECB DPE ABS | ECB 2SC ABS | DRP EAR % MN | GLF SPT ABS | NLF BLT ABS |
|---|---|---|---|---|---|---|---|---|---|
| TOTAL SUM | REPLIC. | 43 | 13 | 9 | 11 | 7 | 60 | 5 | 1 |
| | LOCS | 10 | 5 | 8 | 11 | 7 | 50 | 5 | 1 |
| | PH42B | 95 | 4 | 5 | 99 | 6 | 100 | 3 | 8 |
| | PHT11 | 102 | 4 | 5 | 99 | 5 | 100 | 3 | 8 |
| | DIFF | 7 | 0 | 0 | 0 | 1 | 0 | 0 | 0 |
| | PR > T | 0.01 | 0.65 | 0.27 | 0.78 | 0.49 | 0.97 | 0.37 | |

*PR > T values are valid only for comparisons with Locs >= 10.

TABLE 4A

PAIRED COMPARISON REPORT
VARIETY #1 = PH42B/PHN46
VARIETY #2 = PHP38/PHN46

| | VAR # | PRM ABS | PRM SHD | BU ACR ABS | BU ACR % MN | MST % MN | TST WT ABS | SDG CGR % MN | EST CNT % MN |
|---|---|---|---|---|---|---|---|---|---|
| TOTAL SUM | 1 | 107 | 113 | 175.4 | 102 | 96 | 55.5 | 95 | 100 |
| | 2 | 109 | 111 | 174.0 | 101 | 100 | 56.4 | 122 | 103 |
| | LOCS | 30 | 27 | 129 | 129 | 129 | 81 | 59 | 89 |
| | REPS | 30 | 27 | 148 | 148 | 150 | 92 | 72 | 105 |
| | DIFF | 1 | 2 | 1.4 | 1 | 4 | 0.9 | 27 | 3 |
| | PROB | .000# | .001# | .401 | .262 | .000# | .000# | .000# | .026+ |

| | VAR # | GDU SHD % MN | GDU SLK % MN | STK CNT % MN | PLT HT % MN | EAR HT % MN | RT LDG % MN | STA GRN % MN | STK LDG % MN |
|---|---|---|---|---|---|---|---|---|---|
| TOTAL SUM | 1 | 103 | 102 | 100 | 100 | 104 | 100 | 116 | 99 |

TABLE 4A-continued

PAIRED COMPARISON REPORT
VARIETY #1 = PH42B/PHN46
VARIETY #2 = PHP38/PHN46

|   | 2 | 102 | 102 | 102 | 99 | 104 | 104 | 115 | 101 |
|---|---|---|---|---|---|---|---|---|---|
|   | LOCS | 35 | 20 | 134 | 69 | 69 | 41 | 65 | 95 |
|   | REPS | 43 | 25 | 159 | 80 | 80 | 52 | 74 | 112 |
|   | DIFF | 1 | 0 | 2 | 1 | 1 | 4 | 2 | 2 |
|   | PROB | .008# | .803 | .020+ | .042+ | .564 | .183 | .668 | .095* |

| | VAR # | BRT STK % MN | GRN APP % MN | DRP EAR % MN | GLF SPT ABS | NLF BLT ABS | EYE SPT ABS | ECB DPE ABS | ECB 2SC ABS |
|---|---|---|---|---|---|---|---|---|---|
| TOTAL SUM | 1 | 103 | 99 | 100 | 3.0 | 8.0 | 4.7 | 99.3 | 6.0 |
|   | 2 | 99 | 101 | 100 | 2.8 | 8.0 | 4.1 | 98.7 | 5.3 |
|   | LOCS | 20 | 24 | 41 | 4 | 1 | 6 | 11 | 7 |
|   | REPS | 25 | 24 | 49 | 4 | 1 | 7 | 11 | 7 |
|   | DIFF | 4 | 2 | 0 | 0.3 | 0.0 | 0.6 | 0.5 | 0.7 |
|   | PROB | .172 | .445 | .624 | .761 |   | .180 | .377 | .426 |

\* = 10% SIG
+ = 5% SIG
# = 1% SIG

TABLE 4B

PAIRED COMPARISON REPORT
VARIETY #1 = PH42B/PHN46
VARIETY #2 = PHT11/PHN46

| | VAR # | PRM | PRM SHD | BU ACR ABS | BU ACR % MN | MST % MN | TST WT ABS | SDG VGR % MN | EST CNT % MN |
|---|---|---|---|---|---|---|---|---|---|
| TOTAL SUM | 1 | 107 | 113 | 173.6 | 102 | 98 | 54.3 | 94 | 100 |
|   | 2 | 106 | 111 | 171.4 | 100 | 95 | 55.4 | 111 | 105 |
|   | LOCS | 29 | 26 | 126 | 126 | 126 | 78 | 53 | 84 |
|   | REPS | 29 | 26 | 143 | 143 | 145 | 88 | 64 | 98 |
|   | DIFF | 1 | 1 | 2.2 | 2 | 3 | 1.1 | 17 | 5 |
|   | PROB | .000# | .010+ | .191 | .069* | .000# | .000# | .000# | .000# |

| | VAR # | GDU SHD % MN | GDU SLK % MN | STK CNT % MN | PLT HT % MN | EAR HT % MN | RT LDG % MN | STA GRN % MN | STK LDG % MN |
|---|---|---|---|---|---|---|---|---|---|
| TOTAL SUM | 1 | 104 | 102 | 100 | 100 | 105 | 100 | 120 | 99 |
|   | 2 | 103 | 101 | 103 | 103 | 108 | 101 | 108 | 99 |
|   | LOCS | 35 | 17 | 133 | 65 | 65 | 42 | 57 | 92 |
|   | REPS | 42 | 20 | 157 | 74 | 74 | 53 | 65 | 108 |
|   | DIFF | 1 | 1 | 3 | 2 | 3 | 1 | 12 | 0 |
|   | PROB | .006# | .094* | .000# | .000# | .005# | .832 | .005# | .666 |

| | VAR # | BRT STK % MN | GRN APP % MN | DRP EAR % MN | GLF SPT ABS | NLF BLT ABS | EYE SPT ABS | ECB DPE ABS | ECB 2SC ABS |
|---|---|---|---|---|---|---|---|---|---|
| TOTAL SUM | 1 | 103 | 94 | 100 | 3.0 | 8.0 | 4.7 | 99.3 | 6.0 |
|   | 2 | 102 | 103 | 100 | 2.5 | 8.0 | 4.4 | 99.5 | 5.0 |
|   | LOCS | 18 | 35 | 49 | 4 | 1 | 6 | 11 | 7 |
|   | REPS | 23 | 38 | 59 | 4 | 1 | 7 | 11 | 7 |
|   | DIFF | 0 | 9 | 0 | 0.5 | 0.0 | 0.3 | 0.2 | 1.0 |
|   | PROB | .780 | .001# | .981 | .182 |   | .562 | .765 | .395 |

\* = 10% SIG
+ = 5% SIG
# = 1% SIG

Deposits

Applicant has made a deposit of at least 2500 seeds of Inbred Corn Line PH42B with the American Type Culture Collection (ATCC), Rockville, Md. 20852 U.S.A., ATCC Deposit No. 97647. The seeds deposited with the ATCC on Jul. 8, 1996 were taken from the deposit maintained by Pioneer Hi-Bred International, Inc., 700 Capital Square, 400 Locust Street, Des Moines, Iowa 50309-2340 since prior to the filing date of this application. This deposit of the Inbred Corn Line PH42B will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. §§1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of its rights granted under this patent or under the Plant Variety Protection Act (7 USC 2321 et seq.). Applicant has applied for U.S. Plant Variety Protection of PH42B under Application No. 9600201.

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant inbred and the like may be practiced within the scope of the invention, as limited only by the scope of the appended claims.

What is claimed is:

1. Seed of maize inbred line designated PH42B and having ATCC Accession No. 97647.

2. A maize plant and its parts produced by the seed of claim 1 and its plant parts.

3. Pollen of the plant of claim 2.

4. An ovule of the plant of claim 2.

5. A maize plant having all the physiological and morphological characteristics of the maize plant named PH42B, the seed of which have been deposited under ATCC Accession No. 97647.

6. A male sterile maize plant otherwise having all the physiological and morphological characteristics of the maize plant named PH42B, the seed of which have been deposited under ATCC Accession No. 97647.

7. A tissue culture of regenerable cells of an inbred maize plant PH42B, the seed of which have been deposited under ATCC Accession No. 97647, wherein the tissue culture regenerates plants capable of expressing all the morphological and physiological characteristics of the maize plant named PH42B.

8. The tissue culture of claim 7, the tissue culture selected from the group consisting of leaves, pollen, embryos, roots, root tips, anthers, silks, flowers, kernels, ears, cobs, husks, stalks, cells and protoplasts thereof.

9. A maize plant regenerated from the tissue culture of claim 7, capable of expressing all the morphological and physiological characteristics of inbred PH42B, the seed of which have been deposited under ATCC Accession No. 97647.

10. A method for producing first generation ($F_1$) hybrid maize seed comprising crossing a first inbred parent maize plant with a second inbred parent maize plant and harvesting the resultant first generation ($F_1$) hybrid maize seed, wherein said first or second parent maize plant is the maize plant of claim 2.

11. The method of claim 10 wherein inbred maize plant PH42B, the seed of which have been deposited under ATCC Accession No. 97647, is the female parent.

12. The method of claim 10 wherein inbred maize plant PH42B, the seed of which have been deposited under ATCC Accession No. 97647, is the male parent.

13. An $F_1$ hybrid seed grown therefrom produced by crossing an inbred maize plant according to claim 2 with another, different maize plant.

14. An $F_1$ hybrid plant and its parts grown from the seed of claim 13.

* * * * *